United States Patent
Hu et al.

(10) Patent No.: US 9,402,572 B2
(45) Date of Patent: Aug. 2, 2016

(54) DIGITAL PORTABLE PULSE OXIMETER AND BATTERY-POWERED CONTROL METHOD THEREOF

(75) Inventors: Kun Hu, Qinhuangdao (CN); Yunlong Xu, Qinhuangdao (CN); Ruibin Gao, Qinhuangdao (CN); Zhen Yang, Qinhuangdao (CN); Jinling Zhang, Qinhuangdao (CN); Di Wu, Qinhuangdao (CN); Ruijie Jiang, Qinhuangdao (CN)

(73) Assignee: CONTEC MEDICAL SYSTEMS CO., LTD., Hebei Province (CN)

( * ) Notice: Subject to any disclaimer, the term of this patent is extended or adjusted under 35 U.S.C. 154(b) by 352 days.

(21) Appl. No.: 13/991,617

(22) PCT Filed: Mar. 9, 2012

(86) PCT No.: PCT/CN2012/072120
§ 371 (c)(1),
(2), (4) Date: Jun. 4, 2013

(87) PCT Pub. No.: WO2013/123681
PCT Pub. Date: Aug. 29, 2013

(65) Prior Publication Data
US 2014/0194712 A1    Jul. 10, 2014

(30) Foreign Application Priority Data

Feb. 20, 2012  (CN) .......................... 2012 1 0038577

(51) Int. Cl.
*A61B 5/1455* (2006.01)
*A61B 5/00* (2006.01)

(52) U.S. Cl.
CPC ........... *A61B 5/14552* (2013.01); *A61B 5/6826* (2013.01); *A61B 2560/0204* (2013.01)

(58) Field of Classification Search
None
See application file for complete search history.

(56) References Cited

U.S. PATENT DOCUMENTS 4,163,261 A * 7/1979 Ito .......................... G03B 19/26
                                                        360/13
4,411,274 A * 10/1983 Wright ................... A61B 5/117
                                                        128/903

(Continued)

FOREIGN PATENT DOCUMENTS

CN    201108427 Y    9/2008
CN    201675934 U    12/2010

OTHER PUBLICATIONS

Chinese International Search Report of international application No. PCT/CN2011/072034, dated Nov. 22, 2012.

*Primary Examiner* — Tse Chen
*Assistant Examiner* — Marjan Fardanesh
(74) *Attorney, Agent, or Firm* — J.C. Patents (57) ABSTRACT

The present invention relates to a digital portable pulse oximeter and battery-powered control method thereof. The automatic switching of the power supply is achieved by adding a Hall circuit, and the data displayed is allowed to always face the users by adding an acceleration sensor to the circuit. The advantageous effects of the present invention compared with the prior art are: Users can always read the data from the front side no matter which way they move. The digital portable pulse oximeter of the present invention can be automatically turned on just by inserting a finger, without having to press the switch button, and cut off the power supply by pulling out the finger, as well as judge intelligently whether to continue the measurement after the finger has been pulled out. If yes, the power supply will stay on, which reduces the energy waste and low efficiency caused by the restarting program initialization, improves the use efficiency of the battery and prolongs the battery life.

7 Claims, 4 Drawing Sheets

(56) References Cited

U.S. PATENT DOCUMENTS

| | | | |
|---|---|---|---|
| 5,115,232 A * | 5/1992 | Iizuka | G09G 3/3685 345/213 |
| 5,490,523 A * | 2/1996 | Isaacson | A61B 5/02427 600/323 |
| 5,692,505 A | 12/1997 | Fouts | 128/633 |
| 6,496,711 B1 * | 12/2002 | Athan | A61B 5/14551 600/322 |
| 6,584,336 B1 * | 6/2003 | Ali | A61B 5/14551 600/323 |
| 6,970,792 B1 | 11/2005 | Diab | 702/32 |
| 2004/0249299 A1 | 12/2004 | Cobb | 600/529 |
| 2008/0081973 A1 | 4/2008 | Hoarau | 600/336 |

* cited by examiner

Fig. 4

DIGITAL PORTABLE PULSE OXIMETER AND BATTERY-POWERED CONTROL METHOD THEREOF

FIELD OF THE INVENTION

The invention relates to the medical device field, and more particularly, to a digital portable pulse oximeter and battery-powered control method thereof. The automatic switching of the power supply is achieved by adding a Hall circuit, and the data displayed is allowed to always face the users by adding an orientation sensor to the circuit.

BACKGROUND ART

A pulse oximeter is a non-invasive medical device for continuously monitoring the blood oxygen saturation of arteries in a human body. As a common device of anesthesia monitoring and intensive care in hospitals, the device has also been widely used in a variety of mobile cares and sleep cares at places other than hospitals. The development of both family and community medical healthcare systems has put forward new requirements on the design and manufacture of pulse oximeters; in particular, it is highly desirable that wearable pulse oximeters that are characterized by low price yet high performance and are widely adaptable to families and medical treatment network at community level are provided.

Today, the pulse oximeters commercially available in the domestic and overseas markets generally fall into two categories—analog type and digital type, which can also be divided into desktop type and portable type. Most of the analog pulse oximeters with complicated circuits are desktop type, and when a desktop pulse oximeter is used, signal is transmitted to the instrument through a finger clamp and cable. It is inconvenient for users to move with cable towed, and the cable also makes the guardianship inconvenient, hereby the using occasions are limited. However, with the development of digital circuit technology, a battery-powered portable pulse oximeter with no cable is widely used. Being battery-powered, the pulse oximeter enters operational state after the power supply is turned on, whereas the pulse oximeter will do futile actions and continue consuming the power supply in a state of power-on when no measurement being carried out, which thereby shortens the effective operational time of battery. At the same time, the display of the portable pulse oximeter is disposed on the finger clamp, so the orientation of the finger clamp changes with the users' move and the data displayed can not face the users, which makes the users' reading difficult.

SUMMARY OF THE INVENTION

The object of this invention is to put forward a technical scheme of a digital portable pulse oximeter and battery-powered control method thereof in view of the above problems. In this technical scheme, the automatic switching of the power supply is achieved by adding a Hall circuit, and the data displayed is allowed to always face the users by adding an acceleration sensor to the circuit.

The object of the present invention is achieved through the technical scheme as described below:

A digital portable pulse oximeter comprising a housing body. The said housing body consists of an upper housing body and a lower housing body. The upper housing body and the lower housing body are disposed such that they are stacked together. One end of both the upper and lower housing body is the measurement end where a finger is placed. A pivot and a reset spring disposed between the upper housing body and the lower housing body enable them to be opened and closed at the measurement end. A display window is disposed at outside of and atop the upper housing body, with a display disposed inside the display window. A power supply battery and a measurement analysis circuit are also disposed in the housing body. The measurement analysis circuit comprises a light-frequency converter, a red infrared light emitting diode, a light-emitting driving circuit and a microprocessor. The microprocessor has a power supply stay-on output pin, the light-frequency converter and the light emitting diode are respectively disposed in the upper housing body and the lower housing body at the measurement end of the housing body. The red infrared light emitting diode connects to the light-emitting driving circuit, the interface circuit of the microprocessor connects to the light-emitting driving circuit, the light-frequency converter and the display, respectively; Wherein, an acceleration sensor and a power supply switching-control circuit are also disposed in the housing body, the electrical signal of the acceleration sensor connects to the interface circuit of the microprocessor, the power supply switching-control circuit comprises a Hall switch sensor, a magnet and a switch circuit. The Hall switch sensor and the magnet are respectively disposed in the upper housing body and the lower housing body at the measurement end of the housing body, the magnet induces the output pin of the Hall switch sensor to generate a high-low potential change through the opening and closing of the upper housing body and the lower housing body, the switch circuit includes a dual-input logic control gate circuit and a power switch device, the output pin of the Hall switch sensor connects to one input end of the dual-input logic control gate circuit, the power supply stay-on output pin of the microprocessor connects to the other input end of the dual-input logic control gate circuit, the output end of the dual-input logic control gate circuit connects to the control pin of the power switch device, the input of the power switch device connects to the power supply battery, and the outputs of the power switch device connect to the measurement analysis circuit and the display.

The dual-input logic control gate circuit consists of four dual-input NAND gates, which are the first dual-input NAND gate, the second dual-input NAND gate, the third dual-input NAND gate and the fourth dual-input NAND gate, respectively. The two input ends of the first dual-input NAND gate connect to the output pin of the Hall chip after they are shorted, the output of the first dual-input NAND gate connects to one input of the second dual-input NAND gate, the other input of the second dual-input NAND gate connects to the output of the fourth dual-input NAND gate, the two input ends of the third-dual NAND gate connect to the output of the second dual-input NAND gate after they are shorted out, the output of the second dual-input NAND gate simultaneously connects to one input of the fourth dual-input NAND gate, the other input of the fourth dual-input NAND gate connects to the power supply stay-on output pin of the microprocessor, and the output of the third dual-input NAND gate connects to the control pin of the power switch device, the said power switch device is a P-channel power FET.

After they are shorted out, the two input ends of the first dual-input NAND gate connect to a 100K ohmics resistance and a magnetic bead concatenated in series. One end of the magnetic bead connects to the negative pole of the battery, and the concatenated end of the magnetic bead and the resistance is the negative pole of the power supply of the measurement analysis circuit.

A digital portable pulse oximeter power supply control method comprising a housing body consisting of an upper housing body and a lower housing body, which are disposed such that they are stacked together, one end of both the upper housing body and the lower housing body is a measurement end where a finger is placed, a pivot and a reset spring are disposed between the upper housing body and the lower housing body enabling them to be opened and closed at the measurement end, a power supply battery and a measurement analysis circuit are disposed in the housing body, the measurement analysis circuit comprises a microprocessor having a power supply stay-on output pin. A Hall switch sensor, a magnet and a switch circuit are also disposed in the housing body, the Hall switch sensor and the magnet are respectively disposed in the upper housing body and the lower housing body at the measurement end of the housing body, the magnet induces the output pin of the Hall switch sensor to generate a high-low potential change through the opening and closing of the upper housing body and the lower housing body, the switch circuit includes a dual-input logic control gate circuit and a power switch device, the output pin of the Hall switch sensor connects to one input end of the dual-input logic control gate circuit, the power supply stay-on output pin of the microprocessor connects to the other input end of the dual-input logic control gate circuit, the output end of the dual-input logic control gate circuit connects to the control pin of the power switch device, the input of the power switch device connects to the power supply battery, and the output of the power switch device connects to the measurement analysis circuit of the oximeter, the said power supply control method is:

a. The battery powers the measurement analysis circuit and the display of the oximeter, i.e., the upper housing body and the lower housing body of the oximeter at the measuring end are opened, the output pin of the Hall switch sensor generates a high potential, which causes the output of the dual-input logic control gate circuit to control the power switch device into conduction;

b. Within a certain time, the microprocessor determines whether a blood oxygen signal is measured, i.e., whether a finger has ever been placed in the oximeter within a certain time.

b1. If there is a blood oxygen signal measured, the power supply will stay on, i.e., the power supply stay-on output pin of the microprocessor outputs a power supply stay-on signal;

b2. If there is no blood oxygen signal measured, a signal requiring to cut off the power supply will be sent out, i.e., the power supply stay-on output pin of the microprocessor outputs a signal of cutting off the power supply stay-on;

c. The microprocessor determines whether the upper housing body and the lower housing body at the measurement end of the oximeter housing body are still open; That is, whether the output pin of the Hall chip is still generating a high potential.

c1. If the output pin of the Hall switch sensor generates a high potential, the power supply will stay on;

c2. If the output pin of the Hall switch sensor generates a low potential, the output of the dual-input logic control gate circuit will control the power switch device into non-conduction, and the power supply will be cut off.

The said certain time is 5 seconds.

The advantageous effects of the present invention compared with the prior art are: The users can always read the data from the front side no matter which way they move; The present invention can turn on the pulse oximeter automatically just by inserting a finger, without having to press the switch button, and cut off the power supply by pulling out the finger, as well as judge intelligently whether to continue the measurement after the finger has been pulled out. If yes, the power supply will stay on, which reduces the energy waste and low efficiency caused by the restarting program initialization, improves the use efficiency of the battery and prolongs the battery usage time.

Bellow, the present invention will be described in detail with reference to the drawings and embodiments.

DESCRIPTION OF THE PREFERRED EMBODIMENT

Embodiment 1

Figure 1:
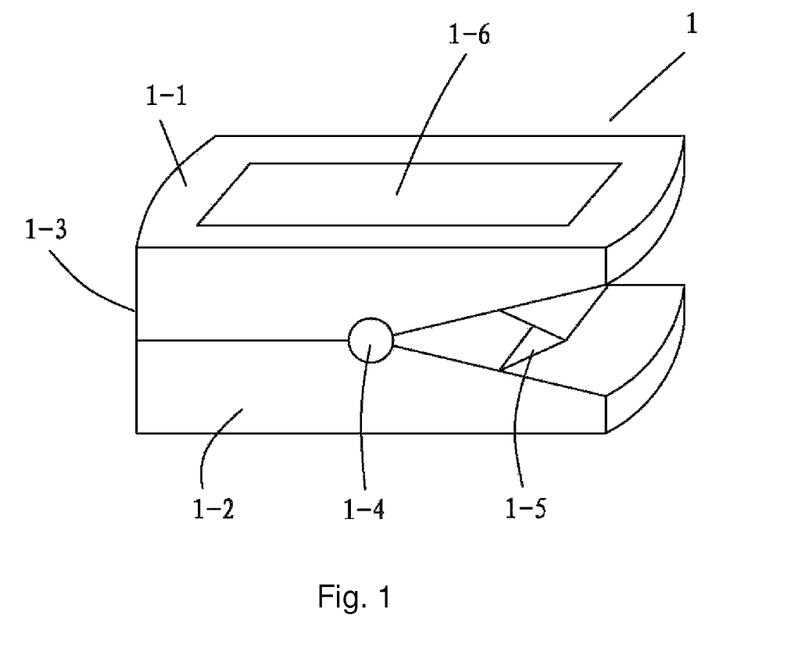
FIG. 1 is a schematic diagram of this invention.
Figure 2:
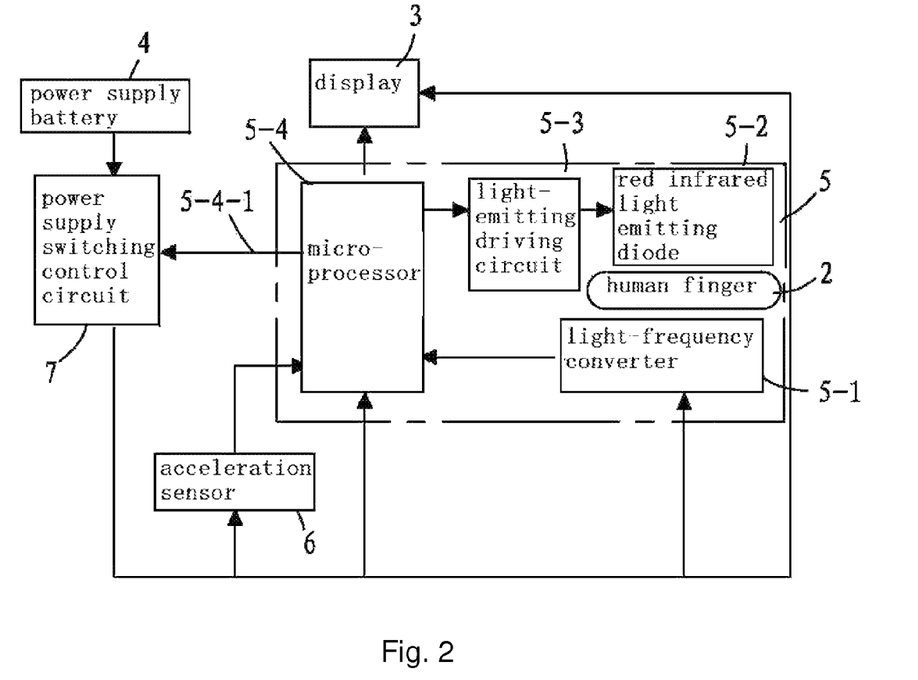
FIG. 2 is a circuit diagram of this invention.
Figure 3:
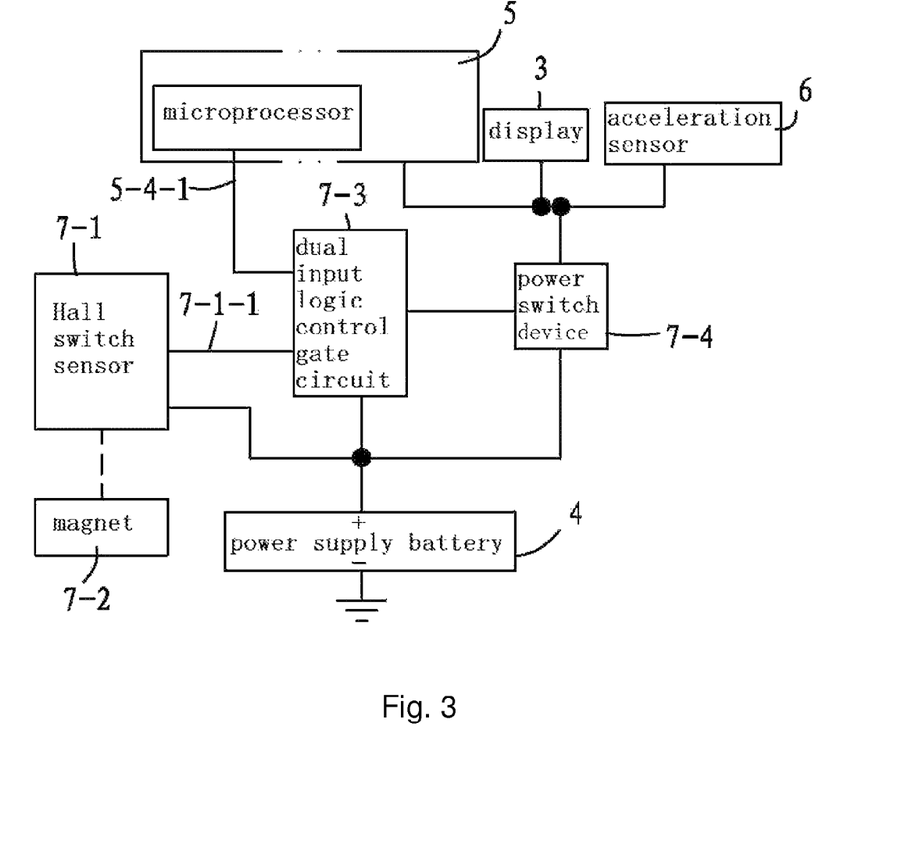
FIG. 3 is a diagram of the power supply switching-control circuit of this invention.
Figure 4:
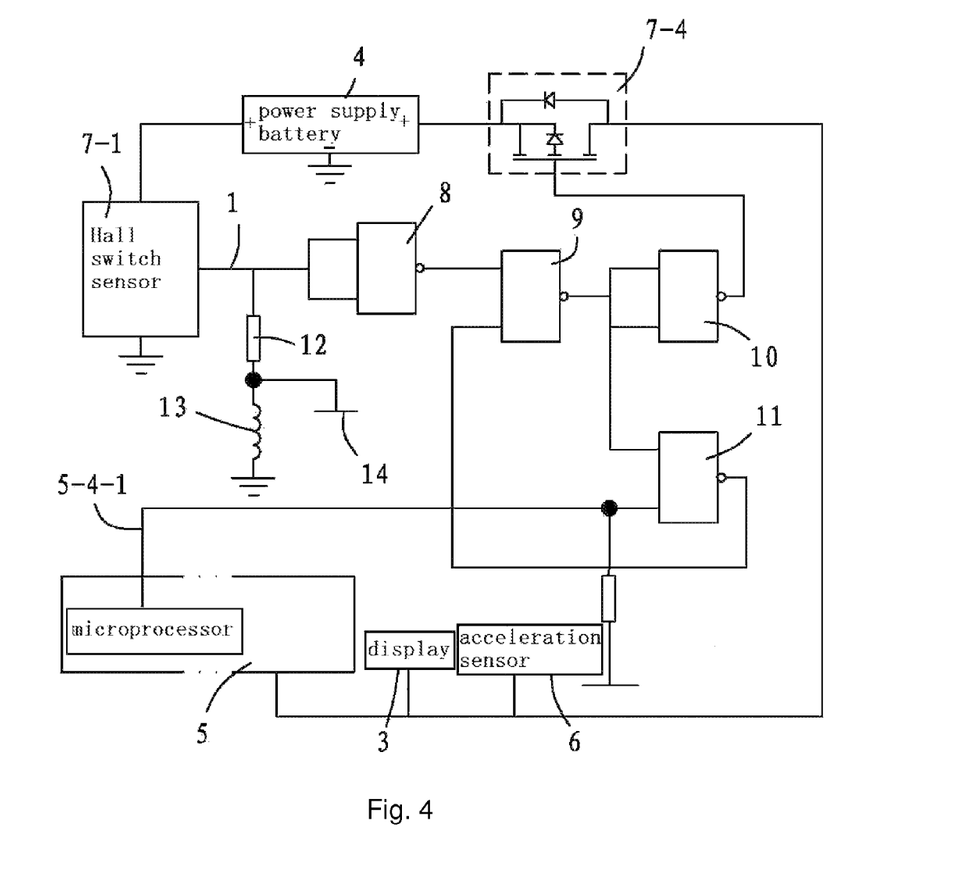
FIG. 4 is a circuit diagram of this invention with a specific power supply switch circuit.

Referring to FIG. 1 and FIG. 2, an embodiment of the digital portable pulse oximeter comprising a housing body 1. The said housing body consists of an upper housing body 1-1 and a lower housing body 1-2. The upper housing body and the lower housing body are disposed such that they are stacked together. One end of both the upper and lower housing body is the measurement end 1-3 where a finger 2 is placed. A pivot 1-4 and a reset spring 1-5 disposed between the upper housing body and the lower housing body enable them to be opened and closed at the measurement end. A display window 1-6 is disposed at outside of and atop the upper housing body, with a display 3 disposed inside the display window. A power supply battery 4 and a measurement analysis circuit 5 are also disposed in the housing body. The measurement analysis circuit comprises a light-frequency converter 5-1, a red infrared light emitting diode 5-2, a light-emitting driving circuit 5-3 and a microprocessor 5-4. The microprocessor has a power supply stay-on output pin 5-4-1, the light-frequency converter and the light emitting diode are respectively disposed in the upper housing body and the lower housing body at the measurement end of the housing body. The red infrared light emitting diode connects to the light-emitting driving circuit, the interface circuit of the microprocessor connects to the light-emitting driving circuit, the light-frequency converter and the display, respectively; wherein, an acceleration sensor 6 and a power supply switching-control circuit 7 are also disposed in the housing body, the electrical signal of the acceleration sensor connects to the interface circuit of the microprocessor. Referring to FIG. 3 and FIG. 4, the power supply switching-control circuit comprises a Hall switch sensor 7-1, a magnet 7-2 and a power supply switch circuit. The Hall switch sensor and the magnet are respectively disposed in the upper housing body and the lower housing body at the measurement end of the housing body, the magnet induces the output pin of the Hall switch sensor to generate a high-low potential change through the opening and closing of the upper housing body and the lower housing body, the power supply switch circuit includes a dual-input logic control gate circuit 7-3 and a power switch device 7-4, the output pin 7-1-1 of the Hall switch sensor connects to one input end of the dual-input logic control gate circuit, the power supply stay-on output pin of the microprocessor connects to the other input end of the dual-input logic control gate circuit, the output end of the dual-input logic control gate circuit connects to the control pin of the power switch device, the input of the power switch device connects to the power supply battery, and the outputs of the power switch device connect to the measurement analysis circuit, the display and the acceleration sensor.

The dual-input logic control gate circuit consists of four dual-input NAND gates, which are the first dual-input NAND gate 8, the second dual-input NAND gate 9, the third dual-input NAND gate 10 and the fourth dual-input NAND gate 11, respectively. The two input ends of the first dual-input NAND gate connect to the output pin of the Hall chip after they are shorted out, the output of the first dual-input NAND gate connects to one input of the second dual-input NAND gate, the other input of the second dual-input NAND gate connects to the output of the fourth dual-input NAND gate, the two input ends of the third-dual NAND gate connect to the output of the second dual-input NAND gate after they are shorted out, the output of the second dual-input NAND gate simultaneously connects to one input of the fourth dual-input NAND gate, the other input of the fourth dual-input NAND gate connects to the power supply stay-on output pin of the microprocessor, and the output of the third dual-input NAND gate connects to the control pin of the power switch device, the said power switch device is a P-channel power FET.

In order to protect the measurement analysis circuit from the interference of the peripheral 50 Hz magnetic field, in this embodiment, the two input ends of the first dual-input NAND gate, after they are shorted out, connect to the 100K ohmics resistance 12 and the magnetic bead 13 concatenated in series. One end of the magnetic bead connects to the negative pole of the battery, and the concatenated end of the magnetic bead and the resistance is the negative pole 14 of the power supply of the measurement analysis circuit; Wherein, the magnetic bead is a plug-in magnetic bead, which is sized to allow a 500 mA current to produce a 30 ohmics impedance.

The acceleration sensor described in the embodiment employs either the SMB380 model or the MMA7455L model. The direction-selecting function achieved by the acceleration sensor of the present embodiment is different from that of the similar products utilizing optical direction sensors. The present acceleration sensor is a triaxial acceleration sensor with a high sensitivity, the operational voltage is 1.7V to 3.6V, which avoids the cumbersome design of the similar acceleration sensors that need a stable power supply. No LDO output is needed, the cost is controlled, and the circuit design space is saved. The acceleration sensor of the present embodiment needs no soft\hardware calibration and can identify the directions automatically, which eliminates the drawback of having to calibrate the acceleration sensor in different regions; The acceleration sensor of the present embodiment is also featured by a quick response, a high sensitivity, a low power consumption, and a simple circuit connection and so on.

The model of the power switch device in the embodiment is SI2301DS FET.

The model of the Hall switch sensor in the embodiment is BU52011HFV Hall device.

Embodiment 2

Referring to embodiment 1, the contents disclosed in embodiment 1 should also be regarded as the contents of the present embodiment. A digital portable pulse oximeter power supply control method comprising a housing body consisting of an upper housing body and a lower housing body, which are disposed such that they are stacked together, one end of both the upper housing body and the lower housing body is a measurement end where a finger is placed, a pivot and a reset spring are disposed between the upper housing body and the lower housing body enabling them to be opened and closed at the measurement end, a power supply battery and a measurement analysis circuit are disposed in the housing body, the measurement analysis circuit comprises a microprocessor having a power supply stay-on output pin; A Hall switch sensor, a magnet and a switch circuit are also disposed in the housing body, the Hall switch sensor and the magnet are respectively disposed in the upper housing body and the lower housing body at the measurement end of the housing body, the magnet induces the output pin of the Hall switch sensor to generate a high-low potential change through the opening and closing of the upper housing body and the lower housing body, the switch circuit includes a dual-input logic control gate circuit and a power switch device, the output pin of the Hall switch sensor connects to one input end of the dual-input logic control gate circuit, the power supply stay-on output pin of the microprocessor connects to the other input end of the dual-input logic control gate circuit, the output end of the dual-input logic control gate circuit connects to the control pin of the power switch device, the input of the power switch device connects to the power supply battery, and the output of the power switch device connects to the measurement analysis circuit of the oximeter, the said power supply control method is:

a. The battery powers the measurement analysis circuit and the display of the oximeter, i.e., the upper housing body and the lower housing body of the oximeter at the measuring end are opened, the output pin of the Hall switch sensor generates a high potential, which causes the output of the dual-input logic control gate circuit to control the power switch device into conduction;

b. Within a certain time, the microprocessor determines whether a blood oxygen signal is measured, i.e., whether a finger has ever been placed in the oximeter within a certain time;

b1. If there is a blood oxygen signal measured, the power supply will stay on, i.e., the power supply stay-on output pin of the microprocessor outputs a power supply stay-on signal;

b2. If there is no blood oxygen signal measured, a signal requiring to cut off the power supply will be sent out, i.e., the power supply stay-on output pin of the microprocessor outputs a signal of cutting off the power supply stay-on;

c. The microprocessor determines whether the upper housing body and the lower housing body at the measurement end of the oximeter housing body are still open; that is, whether the output pin of the Hall chip is still generating a high potential;

c1. If the output pin of the Hall switch sensor generates a high potential, the power supply will stay on;

c2. If the output pin of the Hall switch sensor generates a low potential, the output of the dual-input logic control gate circuit will control the power switch device into non-conduction, and the power supply will be cut off.

The dual-input logic control gate circuit consists of four dual-input NAND gates, which are the first dual-input NAND gate, the second dual-input NAND gate, the third dual-input NAND gate and the fourth dual-input NAND gate, respectively; The two input ends of the first dual-input NAND gate connect to the output pin of the Hall chip after they are shorted out, the output of the first dual-input NAND gate connects to one input of the second dual-input NAND gate, the other input of the second dual-input NAND gate connects to the output of the fourth dual-input NAND gate, the two input ends of the third-dual NAND gate connect to the output of the second dual-input NAND gate after they are shorted out, the output of the second dual-input NAND gate simultaneously connects to one input of the fourth dual-input NAND gate, the other input of the fourth dual-input NAND gate connects to the power supply stay-on output pin of the microprocessor, and the output of the third dual-input NAND gate connects to the control pin of the power switch device, the said power switch device is a P-channel power FET.

The said certain time in the embodiment is 5 seconds, i.e., when no blood oxygen signal is detected within 5 seconds, if the upper housing body and the lower housing body are closed at this point, the oximeter will shut down, and if the upper housing body and the lower housing body remain open, it indicates that the test is continuing, and the oximeter will continue operate, which avoids the repeated boot processes in continuous tests, saves the program initialization time, and improves the service efficiency of the battery and the operational efficiency of the instrument.

What is claimed is:

1. A digital portable pulse oximeter comprising:
   a housing body having an upper housing body and a lower housing body, which are disposed such that they are stacked together, one end of both the upper housing body and the lower housing body being a measurement end where a finger is placed;
   a pivot and a reset spring being disposed between the upper housing body and the lower housing body enabling them to be opened and closed at the measurement end;
   a display window being disposed at outside of and atop the upper housing body, a display being disposed inside the display window;
   a power supply battery; and
   a measurement analysis circuit being disposed in the housing body, the measurement analysis circuit comprising a light-frequency converter, an infrared light emitting diode, a light-emitting driving circuit and a microprocessor;
   the microprocessor having a power supply stay-on output pin, the light-frequency converter and the light emitting diode being respectively disposed in the upper housing body and the lower housing body at the measurement end of the housing body;
   the infrared light emitting diode connecting to the light-emitting driving circuit, the interface circuit of the microprocessor connecting to the light-emitting driving circuit, the light-frequency converter and the display, respectively, wherein an acceleration sensor and a power supply switching-control circuit are also disposed in the housing body, the electrical signal of the acceleration sensor connects to the interface circuit of the microprocessor,
   wherein said power supply switching-control circuit comprises a Hall switch sensor, a magnet and a switch circuit, the Hall switch sensor and the magnet are respectively disposed in the upper housing body and the lower housing body at the measurement end of the housing body, said magnet induces the output pin of the Hall switch sensor to generate a high-low potential change through the opening and closing of the upper housing body and the lower housing body, the switch circuit includes a dual-input logic control gate circuit and a power switch device, the output pin of the Hall switch sensor connects to one input end of the dual-input logic control gate circuit, the power supply stay-on output pin of the microprocessor connects to the other input end of the dual-input logic control gate circuit, the output end of the dual-input logic control gate circuit connects to the control pin of the power switch device, the input of the power switch device connects to the power supply battery, and the outputs of the power switch device connect to the measurement analysis circuit and the display.

2. The digital portable pulse oximeter as claimed in claim 1, wherein the dual-input logic control gate circuit consists of four dual-input NAND gates, which are the first dual-input NAND gate, the second dual-input NAND gate, the third dual-input NAND gate and the fourth dual-input NAND gate, respectively; the two input ends of the first dual-input NAND gate connect to the output pin of the Hall chip after they are shorted out, the output of the first dual-input NAND gate connects to one input of the second dual-input NAND gate, the other input of the second dual-input NAND gate connects to the output of the fourth dual-input NAND gate, the two input ends of the third-dual NAND gate connect to the output of the second dual-input NAND gate after they are shorted out, the output of the second dual-input NAND gate simultaneously connects to one input of the fourth dual-input NAND gate, the other input of the fourth dual-input NAND gate connects to the power supply stay-on output pin of the microprocessor, and the output of the third dual-input NAND gate connects to the control pin of the power switch device, the said power switch device is a P-channel power FET.

3. The digital portable pulse oximeter as claimed in claim 2, wherein the input ends of the first dual-input NAND gate connect to a 100K ohmics resistance and a magnetic bead concatenated in series, one end of the magnetic bead connects to the negative pole of the battery, and the concatenated end of the magnetic bead and the resistance is the negative pole of the power supply of the measurement analysis circuit.

4. A digital portable pulse oximeter power supply control method comprising providing the digital portable pulse oximeter according to claim 1, wherein:
   a. the battery powers the measurement analysis circuit and the display of the oximeter, the upper housing body and the lower housing body of the oximeter at the measuring end are opened, the output pin of the Hall switch sensor generates a high potential, which causes the output of the dual-input logic control gate circuit to control the power switch device into conduction;
   b. within a certain time, the microprocessor determines whether a blood oxygen signal is measured, whether a finger has ever been placed in the oximeter within a certain time;
   b1. if there is a blood oxygen signal measured, the power supply will stay on, the power supply stay-on output pin of the microprocessor outputs a power supply stay-on signal;
   b2. if there is no blood oxygen signal measured, a signal requiring to cut off the power supply will be sent out, the power supply stay-on output pin of the microprocessor outputs a signal of cutting off the power supply stay-on;
   c. the microprocessor determines whether the upper housing body and the lower housing body at the measurement end of the oximeter housing body are still open, whether the output pin of the Hall chip is still generating a high potential;
   c1. if the output pin of the Hall switch sensor generates a high potential, the power supply will stay on;
   c2. if the output pin of the Hall switch sensor generates a low potential, the output of the dual-input logic control gate circuit will control the power switch device into non-conduction, and the power supply will be cut off.

5. The digital portable pulse oximeter power supply control method as claimed in claim 4, wherein the said certain time is 5 seconds.

6. The digital portable pulse oximeter power supply control method as claimed in claim 4, wherein the dual-input logic control gate circuit consists of four dual-input NAND gates, which are the first dual-input NAND gate, the second dual-input NAND gate, the third dual-input NAND gate and the fourth dual-input NAND gate, respectively; the two input ends of the first dual-input NAND gate connect to the output pin of the Hall chip after they are shorted out, the output of the first dual-input NAND gate connects to one input of the second dual-input NAND gate, the other input of the second dual-input NAND gate connects to the output of the fourth dual-input NAND gate, the two input ends of the third-dual NAND gate connect to the output of the second dual-input NAND gate after they are shorted out, the output of the second dual-input NAND gate simultaneously connects to one input of the fourth dual-input NAND gate, the other input of the fourth dual-input NAND gate connects to the power supply stay-on output pin of the microprocessor, and the output of the third dual-input NAND gate connects to the control pin of the power switch device, the said power switch device is a P-channel power FET.

7. The digital portable pulse oximeter as claimed in claim 1, wherein the acceleration sensor enables the data displayed to always face the users.

\* \* \* \* \*